(12) United States Patent
Ganz et al.

(10) Patent No.: US 7,107,996 B2
(45) Date of Patent: Sep. 19, 2006

(54) APPARATUS AND METHOD FOR TREATING ATHEROSCLEROTIC VASCULAR DISEASE THROUGH LIGHT STERILIZATION

(76) Inventors: Robert A. Ganz, 13956 Emerald Ridge, Minnetonka, MN (US) 55305; Brian D. Zelickson, 2764 Drew Ave. South, Minneapolis, MN (US) 55416

( * ) Notice: Subject to any disclaimer, the term of this patent is extended or adjusted under 35 U.S.C. 154(b) by 280 days.

(21) Appl. No.: 10/298,724

(22) Filed: Nov. 18, 2002

(65) Prior Publication Data

US 2003/0097122 A1 May 22, 2003

Related U.S. Application Data

(63) Continuation-in-part of application No. 10/119,855, filed on Apr. 9, 2002, now Pat. No. 6,764,501.

(60) Provisional application No. 60/364,976, filed on Mar. 15, 2002, provisional application No. 60/282,780, filed on Apr. 10, 2001.

(51) Int. Cl.
*A61B 19/00* (2006.01)

(52) U.S. Cl. .............................. 128/898; 606/7; 607/88; 607/89; 433/29

(58) Field of Classification Search ................ 128/898; 606/2, 7, 13–16; 607/88, 89, 92; 433/25, 433/29
See application file for complete search history.

(56) References Cited

U.S. PATENT DOCUMENTS

| | | | |
|---|---|---|---|
| 4,773,899 A | 9/1988 | Spears | |
| 4,848,336 A | 7/1989 | Fox et al. | |
| 4,998,930 A | 3/1991 | Lundahl | |
| 5,041,108 A | 8/1991 | Fox et al. | |
| 5,059,191 A | 10/1991 | Beyer et al. | |
| 5,188,632 A | 2/1993 | Goldenberg | |
| RE34,544 E * | 2/1994 | Spears | 604/20 |
| 5,334,171 A | 8/1994 | Kaldany | |
| 5,405,369 A | 4/1995 | Selman et al. | |
| 5,531,662 A | 7/1996 | Carr | |
| 5,591,199 A | 1/1997 | Porter et al. | |
| 5,637,877 A | 6/1997 | Sinofsky | |
| 5,647,840 A | 7/1997 | D'Amelio et al. | |
| 5,653,683 A | 8/1997 | D'Andrea | |
| 5,658,148 A | 8/1997 | Neuberger | |
| 5,718,577 A * | 2/1998 | Oxman et al. | 433/37 |
| 5,741,246 A | 4/1998 | Prescott | |
| 5,769,844 A | 6/1998 | Ghaffari | |

(Continued)

FOREIGN PATENT DOCUMENTS

JP 10-94583 4/1998

OTHER PUBLICATIONS

U.S. Appl. No. 09/338,687, filed Jun. 23, 1999, Ganz.

(Continued)

*Primary Examiner*—A. Farah
(74) *Attorney, Agent, or Firm*—James V. Harmon

(57) ABSTRACT

A method and apparatus for treating gum disease includes a light producing dental appliance that is accessible exteriorly of the body for placement within the mouth of the patient to expose the mouth to light radiation of a selected wavelength and in an amount that is effective for killing or debilitating pathogenic microorganisms and especially *Porphyromona gingivalis* within the mouth of the patient such that the bacterial load carried to the heart is diminished thereby reducing or eliminating the symptoms of coronary artery disease, atherosclerosis vascular inflammation and plaque formation.

24 Claims, 6 Drawing Sheets

U.S. PATENT DOCUMENTS

| | | | |
|---|---|---|---|
| 5,843,143 | A | 12/1998 | Whitehurst |
| 5,845,640 | A | 12/1998 | Lawandy |
| 5,855,595 | A | 1/1999 | Fujishima et al. |
| 5,871,522 | A | 2/1999 | Sentilles |
| 5,989,283 | A | 11/1999 | Wilkins |
| 6,056,548 | A | 5/2000 | Neuberger |
| 6,061,591 | A | 5/2000 | Freitag et al. |
| 6,070,096 | A | 5/2000 | Hayashi |
| 6,561,808 | B1 * | 5/2003 | Neuberger .................. 433/215 |
| 6,764,501 | B1 * | 7/2004 | Ganz ........................... 607/92 |
| 2004/0127892 | A1 * | 7/2004 | Harris ......................... 606/11 |

OTHER PUBLICATIONS

U.S. Appl. No. 09/598,653, filed Jun. 22, 2000, Ganz.
U.S. Appl. No. 10/119,976, filed Apr. 9, 2002, Ganz et al.
C.E. Millson et al., Ex-Vivo Treatment of Gastric Helico-bacter Infection by Photodynamic Therapy; Journal of Photo-chemistry and Photobiology B: Biology 32 (1996) 59-65 London.
C.E. Millson et al., The Killing of Helicobacter pylori by Low Power Laser Light in the Presence of a Photosensitizer; J Med Microbiology vol. 44 (1996) 245-252.
Martinetto P., et al. Bactercidal Effects Induced by Laser Irradiation and Haematoporphyrin Against Gram-positive and Gram-negative Microorganisms. Drugs exp. Clin Res. XII (4) : 335-342, 1986.
Kubey W., et al. In Vitro Studies on the Microbicidal Effectiveness of a Xenon-based Ultraviolet Light Device for Continuous Ambulatory Peritoneal Connections. Blood Purif. 9 (2) : 102-108, 1991.
U.S. Appl. No. 10/066,162, filed Jan. 31, 2002, Harris.
U.S. Appl. No. 60/410,488, filed Sep. 12, 2002, Harris.
U.S. Appl. No. 60/464,929, filed Apr. 22, 2003, Harris.

* cited by examiner

APPARATUS AND METHOD FOR TREATING ATHEROSCLEROTIC VASCULAR DISEASE THROUGH LIGHT STERILIZATION

The present application is a continuation in part of application Ser. No. 10/119,855, filed Apr. 9, 2002, now U.S. Pat. No. 6,764,501, which claims Priority from Provisional application 60/282,780, filed Apr. 10, 2001, and claims benefit of Provisional application 60/364,976, filed Mar. 15, 2002.

FIELD OF THE INVENTION

This invention relates to an apparatus and method for treating atherosclerotic vascular disease and periodontal disease by means of light radiation.

BACKGROUND OF THE INVENTION

Atherosclerotic vascular disease represents one of the major health problems in the world. It is the number one cause of death in the United States, being responsible for one third of all reported mortality on an annual basis. The magnitude of the problem is staggering; in the United States alone over 60 million people have some form of atherosclerotic vascular disease. In 1995, approximately 1,000,000 people died from this problem. Atherosclerotic vascular disease ranks as the leading reason for social security disability, limitation in physical activity, and hospital bed use accounting for 46 million bed days in 1994. The direct and indirect costs of treating this scourge is in the hundreds of billions of dollars on an annual basis.

Although research in this area has been intense, the exact cause of atherosclerotic artery disease remains unknown. Atherosclerosis is the descriptive term for thickened and hardened lesions of the arteries. It results from fatty deposits that build up in the innermost lining, or intima, of the artery. The lesions are generally eccentric and if they become sufficiently large, can occlude the artery and thus the blood supply to a tissue or organ, resulting in ischemia or necrosis. If this occurs, it often leads to the characteristic clinical outcomes of myocardial infarction (heart attack), cerebral infarction (stroke), gangrene of the extremities, etc.

The exact cause of the fatty build-up is not known although the stages of progression are well described and certain risk factors well-identified, such as smoking, high cholesterol levels, obesity, diabetes etc. More recently, evidence has pointed to a potential infectious cause of atherosclerotic vascular disease. *Cytomegalo* virus, *Chlamydia*, *Helicobacter pylori*, and *porphyromona gingivalis* have all been associated with atherosclerotic disease. The infectious pathogens are presumed to cause chronic inflammation, which results in atherosclerotic deposition.

In one study involving *Helicobacter pylori*, 38 atherosclerotic plaques were obtained at carotid endarterctomy, and examined for the presence or absence of bacteria. The researchers used morphological and immunohistochemical techniques to do this, and a highly sensitive polymerase chain reaction method to search for *Helicobacter* DNA. As a control, the researchers examined 7 carotid arteries obtained at autopsy from subjects without carotid atherosclerosis. The researchers detected the presence of *Helicobacter pylori* DNA in 20 out of 38 atheromatous plaques, and morphological/immunohistochemical evidence of bacteria in 10 of the DNA-positive plaques. None of the 7 normal carotid arteries were positive for *Helicobacter pylori* (Ameriso, 2001).

If atherosclerotic artery disease were to be infectious in etiology, antibiotics probably would not work well due to lack of penetration into dense plaque.

Besides the possibility of an infectious etiology, atherosclerosis involves chronic inflammation of the vessels. It is now apparent that chronic systemic inflammatory or infectious conditions, such as chronic gum disease, can lead to up-regulation of inflammatory reactions or proteins such as C-reactive protein. Either the proximate cause of the inflammation, such as the bacteria *Porphyromona gingivalis* in chronic gum disease or the resulting release or up-regulation of the inflammatory condition can spread to the vessels, such as coronary arteries, and cause atherosclerosis without other injurious environmental factors, such as high cholesterol or smoking.

In view of these and other deficiencies of the prior art it is the primary object of the present invention to provide an apparatus and method for treating atherosclerotic vascular disease using light radiation.

Another more specific object is to treat vascular disease of the character described using light radiation without significant damage to the vessel or surrounding body tissue.

A further object of the present invention is to provide an apparatus of the type described which is characterized by emitting radiation which is destructive to pathogenic microorganisms that cause and/or contribute to atherosclerotic disease without producing sufficient heat to damage body tissues.

Yet another object of the invention is to provide an apparatus of the character described which is small enough for insertion into relatively small blood vessels such as the coronary arteries but is also useful for treating blood vessels throughout the body including cerebral vessels and peripheral vessels that are partially or completely occluded by atherosclerotic plaque.

A still further object of the present invention is the provision of a method and apparatus for treating vascular disease and especially coronary artery disease by reducing or eliminating bacterial infections in other parts of the body and especially the mouth.

These and other more detailed and specific objects of the present invention will be better understood by reference to the following figures and detailed description which illustrate by way of example of but a few of the various forms of the invention within the scope of the appended claims.

SUMMARY OF THE INVENTION

Figure 1:
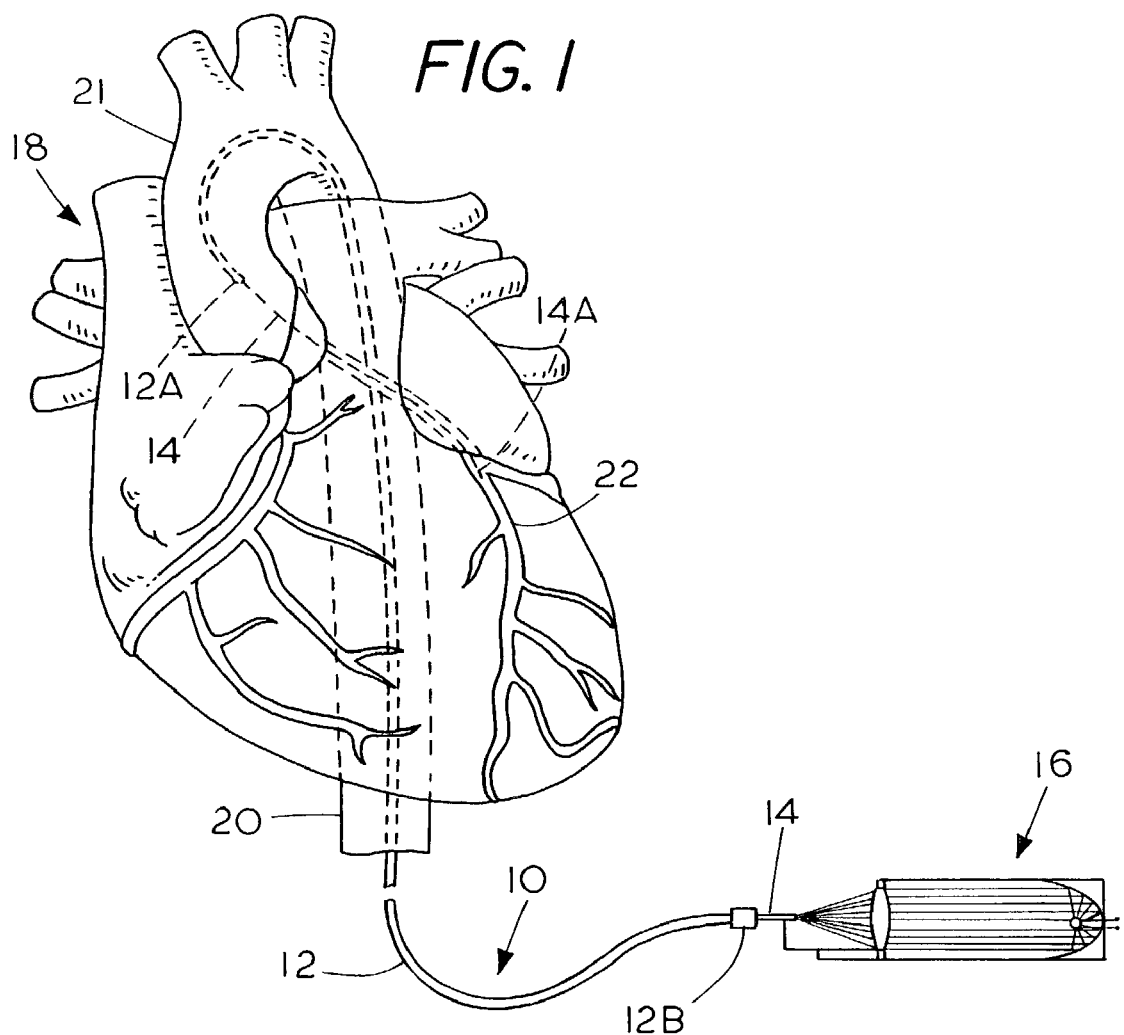
FIG. 1 is a diagrammatic elevational view showing a method and apparatus in accordance with the invention for treating coronary atherosclerosis.

Briefly, the present invention concerns a method and apparatus for eliminating atherosclerotic vascular disease, periodontal disease and associated inflammation by the exposure of the body of the patient, e.g., interior lining of the arteries or other vessels or an exteriorly accessible part of the body, especially the mouth, to visible or ultraviolet light energy of a selected spectrum, to thereby sterilize the vessels or mouth and gums, eradicating infectious pathogens, decreasing inflammation and reversing the pathogenesis of atherosclerotic artery disease.

An apparatus is described for use in the mouth or for insertion into the body of a patient through a blood vessel or affected body tissue for eliminating microorganisms from the interior of the blood vessel or tissue by treating atherosclerosis or its precursor conditions through the application of light energy. The light energy can be supplied through a fiber optic bundle positioned via an intra-arterial catheter that is connected to an appropriate light radiation source located outside of the body during treatment. In another form of the invention, the light energy is produced by means of a light energy source located at the distal tip of the instrument positioned centrally within or adjacent to the atherosclerotic plaque formation during treatment or into or adjacent to tissue in another part of the body. The light source can, for example, be a light emitting diode (LED) or a transparent tube containing a chemical light source or a chemiluminescent substance for producing cool light energy within the body to destroy the pathogenic microorganisms in the surrounding tissue.

The utility of the present invention in the treatment of vascular inflammatory disease is also important not only by killing bacteria or other infectious organisms, but also because the administration of light energy can be useful in reducing inflammation of the tissue. While the theory of operation is not known with certainty, it appears that infection of the vessels, with bacteria or other microorganisms, results in generalized inflammation of the vessels that may eventually lead to atherosclerotic vascular disease and that the exposure of body tissue to light energy such as blue light, red light, or the combination can be useful in reducing inflammation of the vascular tissue even if the pathogenic microorganisms are not killed. The present method of treatment is therefore important because it has been observed that vascular inflammation appears to lead to coronary artery disease and consequently treatment of the inflammation per se can be helpful in reducing or eliminating symptoms of the disease. The present treatment of the vascular inflammation as disclosed herein is also beneficial because reducing inflammation will decrease the presence of inflammatory cytokines and inflammatory chemokines. In addition, it can also reduce the presence of acute phase reactants and soluble adhesion molecule TLR4 receptor activity which is beneficial to the patient. Thus, the present invention can be used to decrease the expansion of adhesion molecules, reduce proliferation of smooth muscle cells and activate immune cells which help to reduce or eliminate the symptoms of vascular inflammatory disease.

DETAILED DESCRIPTION OF THE INVENTION

The therapeutic method in accordance with the present invention is suited for use in various vessels and tissues including, but not limited to, the heart, brain and peripheral vessels and can also be used with various devices, fabrication methods, arrangements, systems and methods of employment which irradiate body tissues including the teeth and gums or the walls of various vessels within the body of a patient by means of light radiation in sufficient amount to debilitate or kill microorganisms lining the vessel or tissue in which the invention is used without significant damage to body tissue.

In order to provide a better understanding, the present invention will be described by way of example in the treatment of coronary artery disease and periodontal disease. It should be understood, however, that the invention is not limited to specific apparatus or methods described. During treatment, light radiation damages the microorganisms e.g. by producing apoptosis or programmed cell death or necrosis in which the DNA of the microorganism is rendered unable to divide. The apoptosis, or necrosis, that occurs in the microorganism prevents it from further replication. Consequently, the microorganisms die by mutation and, in some cases, by the disruption of metabolic processes at the cellular level. Some fraction of the microorganisms may also be killed immediately by the light radiation. An important advantage of the invention lies in the fact that many organisms, such as bacteria and viruses, are exquisitely sensitive to light radiation; sensitive to a much greater degree than the surrounding human cells. The present invention provides a way in which the organism can be killed or debilitated without significant damage or destruction of the host cells.

Figure 2:
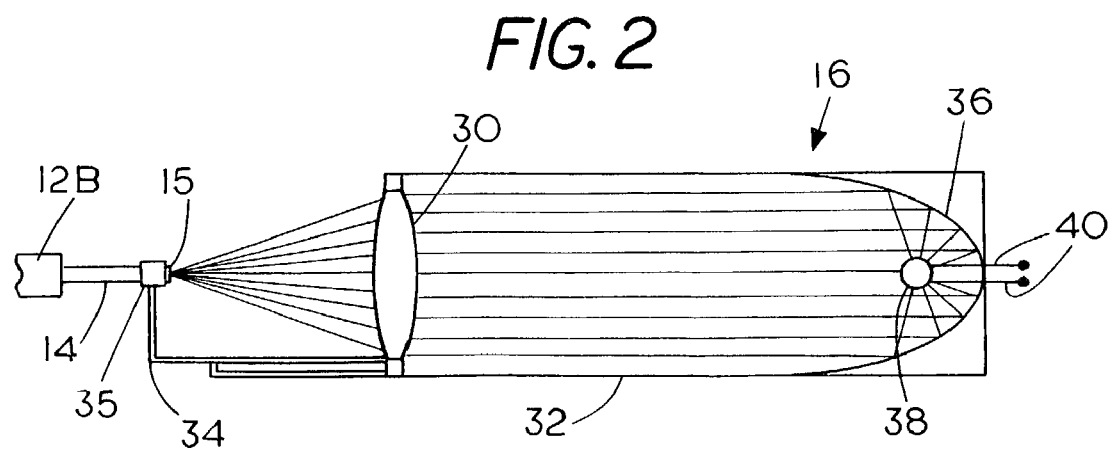
FIG. 2 is an enlarged view of an illumination device used for supplying a light energy for treating the patient.
Figure 3:
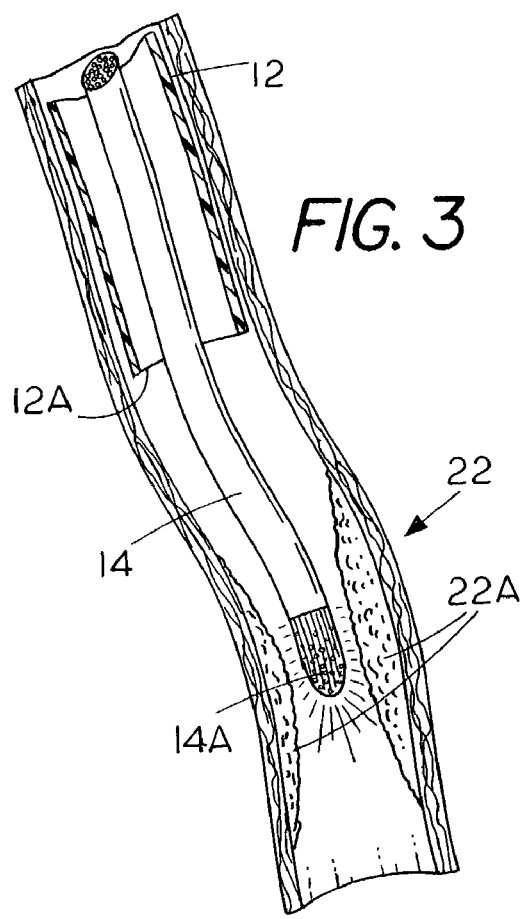
FIG. 3. is a diagrammatic longitudinal sectional view on a greatly enlarged scale showing the distal end of the fiber optic bundle of FIGS. 1 and 2 within a coronary artery.

Refer first to FIGS. 1–3 which illustrate how the present invention utilizes light energy and especially visible or ultraviolet light of a selected spectrum for killing infectious pathogens within the circulatory system so as to sterilize the interior of a blood vessel, artery or vein. Light energy is applied via an apparatus indicated generally by the numeral 10 which includes a fiber optic bundle 14 that may be, for example, about a millimeter in diameter which is delivered through a catheter 12 that is threaded in a manner similar to that now used for diagnosing and treating atherosclerosis and in conducting angioplasty or the placement of a stent. A larger diameter fiber bundle can be used for other operations. In this example, the catheter 12 is introduced through the femoral artery but it could be introduced via the arm or wrist if required. The catheter 12 is shown passing through the aorta 20 and through the aortic arch 21. The catheter 12 is positioned in the aortic arch 21 in the same manner used in angiography for diagnosing the extent of the atherosclerosis. Thus in the method used in the present invention, the catheter 12 is placed in the aortic arch or other artery or vein conventionally. The fiber optic bundle 14 is then passed through the catheter 12, exiting through the distal end of the catheter 12A and is then passed in this example into the coronary artery 22 so that the distal end 14A of the fiber optic bundle 14 is located as shown in FIG. 3 in close proximity to or into the occlusion at the narrow point of the artery 22 containing the atherosclerotic plaque 22A.

The fiber optic bundle 14 can, for example, comprise spun glass bundle having substantial flexibility to allow proper positioning into an artery or vein. A typical fiber bundle 14 can contain as many as 200 separate quartz fibers. To prevent solarization of the fiber optics, the fiber bundle is hydrogen loaded and can be formed from fused quartz provided with an aluminum buffer. One suitable fiber bundle is a UVI or UVM fiber optic bundle manufactured by Polymicro Technologies of Phoenix, Ariz. By using a fiber optic bundle of this composition, minimal attenuation of the radiation occurs within the fiber optic bundle due to solarization. Solarization is an undesirable blackening of the fibers caused by energy absorption.

Refer now especially to FIG. 2. which illustrates the light energy or illumination supply 16 including a glass condensing lens 30 mounted upon a base 32 with a bracket at its left end in the figure supporting a collar 35 to hold the proximal end 15 of the fiber optic bundle 14 which projects somewhat from the proximal end 12B of the catheter 12. The lens 30 focuses collimated light to a point where it enters the fiber optic bundle 14. The fiber bundle is held by the collar 35 at the focal point of the light rays that pass through the lens 30. Light is provided by a light source 38 that is placed at the focal point of a three-dimensional parabolic mirror 36. Power is supplied to the lamp 38 by means of conductors 40.

As shown in FIG. 3, the distal end 14A can be tapered and rounded at its extreme end to expose the ends of the fibers as illustrated enabling light to pass out of the free end of the fiber optic bundle 14 which serves as a light energy distribution head for illuminating the surrounding plaque formation 22A so as to kill or debilitate the pathogenic microorganisms present in the plaque and the vessel without ablation or other damage to the tissue of the body.

A variety of different kinds of light sources can be used including a laser, a source of ultraviolet light such as a low pressure mercury lamp, a source of visible light such as an incandescent lamp, a flash lamp such as a xenon flash lamp, an arc lamp, a combination mercury-xenon lamp, an Excimer laser, a tunable dye laser, laser diode or light emitting diode (LED) which will be described below. Light can also be provided by cool light sources such as chemical or chemiluminscent sources. Although the wavelength of the light use can be varied, preferred ranges are between about 300–500 nm and 600–800 nm along with the combination of such wavelengths. One preferred lamp 38 comprises either an ultraviolet lamp, such as a low pressure mercury vapor lamp, or a flash lamp formed from fused quartz, e.g. a xenon arc flash lamp, that can be made to pulse or flash periodically at selected timed intervals. One suitable flash lamp comprises a filtered short-arc xenon lamp as a radiation source for producing ultraviolet radiation. While radiation at various wavelengths can be used, one preferred range is ultraviolet light of about 200–400 nm. Good results have been obtained in debilitating pathogenic microorganisms with a filtered or non-filtered xenon flash lamp producing UV light between about 240–280 nm having a substantial portion thereof between about 250–270 nm, with a 258 nm peak being optimal for typical pathogenic microorganisms. The flash lamp is operated by a triggered discharge of energy from an electrolytic storage capacitor contained in a suitable power supply (not shown) to produce a very short burst of high intensity light. A computerized control also contained in the power supply actuates a commercially available triggering circuit which causes the xenon gas to suddenly become a low resistance path, at which time the energy stored in the electrolytic capacitor discharges through the flash lamp or tube 38, resulting in a short duration, brilliant burst of visible light radiation that contains ultraviolet light. The computer causes the lamp to flash at selected timed intervals, e.g., every five seconds, but the interval can be changed as desired by reprogramming the computer. The radiation from the lamp is emitted from the end 14A the fiber bundle and spreads out in all directions, to thereby debilitate or kill the pathogenic microorganisms, e.g,. *H. pylori, Chlamydia*, Herpes Virus or *Porphyromona gingivalis* that are present in the vessel or tissue.

During use, the light energy, which can include both visible and ultraviolet light, blankets and penetrates the wall of the vessel 22 from the interior so as to kill any pathogenic microorganisms that exist in the vessel wall 22 or in the plaque 22A itself or tissue.

For various applications, visible light can be used. In one preferred form of the invention, visible blue or red light or the combination is employed. Blue and red light can be produced by an incandescent lamp or other suitable lamp, LED, laser or chemical light source with wavelengths predominantly between about 300 nm to 470 nm, 500–800 nm respectively. An important feature of the present invention is the ability of the light radiation of the distribution head 14A to kill the microorganisms without permanently damaging the body cells or tissue or the inner lining of the artery as previously occurred when gamma or beta radiation was used to prevent restenosis of a coronary artery after angioplasty. While the invention has been described by way of example in treating a coronary artery it can be used on any part of the body that has been damaged by atherosclerosis including peripheral vascular disease, cerebral disease, etc., where microorganisms are a contributing factor to the disease condition or in treating any condition that predisposes the patient to atherosclerosis, e.g., gum disease.

Figure 4:
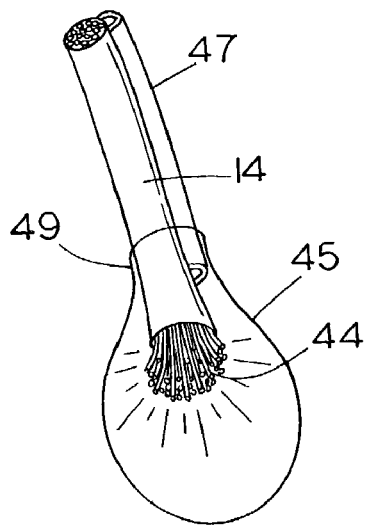
FIG. 4 is a view of a fiber optic bundle as in FIG. 3 with a modified energy distribution head.

Refer now to FIG. 4 which shows a modified form of the invention wherein the distribution head portion 44 of the fiber optic bundle 14 is enlarged somewhat so that the fibers are spread apart and to some degree those near the periphery turn outwardly so as to distribute the light energy more uniformly in all directions. In addition, the distribution head 44 is surrounded by a transparent inflatable balloon 45 into which a saline solution, air or other inflation fluid is introduced through an inflation duct 47. The balloon 45 is securely bonded at 49 to the outer surface of the fiber bundle 14 enclosing the head so that when inflated, the balloon 45 occludes blood flow temporarily to allow better penetration of the light energy from the distribution head 44 into the vessel wall and into the plaque.

Figure 5:
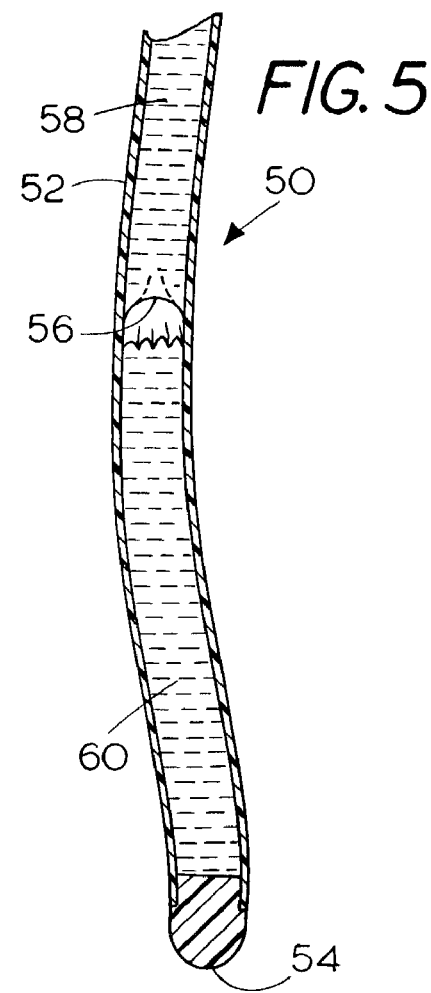
FIG. 5 is a partial longitudinal sectional view of another form of light energy distribution unit.

Refer now to FIG. 5 which shows another form of the invention. In FIG. 5 the fiber optic bundle 14 is replace by a tube 50 having generally the same dimensions as the fiber optic bundle and including a thin, flexible side wall 52 of any suitable transparent plastic composition that can be well tolerated by the body tissue. After the tube 50 has been formed, a flexible plastic film barrier 56 is securely bonded e.g., by adhesive bonding to its inner wall. The barrier 56 is of a weaker plastic film than the wall 52 of the tube 50. Once the barrier 56 is in place, the tube is filled with two chemically reactive chemiluminescence liquids 58 and 60. The distal end of the tube 50 is then sealed with a closure element 54 that can be securely bonded in place e.g., by means of an adhesive or heat. The tube 50 which serves as a light distribution head, is then stored indefinitely until it is to be used. Just before use, the tube is manipulated to apply pressure to the tube in the area of the barrier 56 which deflects the walls inwardly increasing the pressure within the tube enough to cause the barrier 56 to rupture as shown by dotted lines in FIG. 5 allowing the chemically reactive chemiluminescent liquids 58 and 60 to mix, producing a chemical reaction which causes the fluid to luminesce so as to provide a cool light radiation for killing the pathogenic microorganisms within the atherosclerotic vessel or other tissue in the same manner described hereinabove. The light source within the tube 50 is allowed to remain in place within the vessel as long as required to accomplish the desired treatment. In this example, light is produced by a chemical agent or by a chemiluminescent agent. An advantage of using a chemical or chemiluminescent liquid is that the light radiation is of a cool variety which is absorbed by the microorganisms and is lethal to them but produces little if any heat which can be sensed and will not damage surrounding tissue of the patient. A variety of chemiluminescence substances can be employed such as luminal and lucigenin. Among the preferred liquids are the oxilaic ester and hydrogen peroxide with an efficient fluorescer and catalyst as disclosed in U.S. Pat. No. 3,597,362, which is incorporated herein by reference.

Other kinds of fluorescent compounds include: the conjugated polycyclic aromatic compounds examples of which are anthracene, benzanthracene, phenanthrene, naphthacene, pentacene, perylene, perylene violanthrone, and the like and their substituted forms.

Typical substituents for all of these are phenyl, lower alkyl (C.sub.1–C.sub.6), chloro, bromo, cyano, alkoxy (C.sub.1–C.sub.16), and other like substituents which do not interfere with the light-generating reaction can be used.

The preferred fluorescers are 9,10-bis(phenylethynyl) anthracene, 1-methoxy-9, 10-bis(phenylethynyl) anthracene, perylene, 1,5-dichloro 9,10-bis(phenylethynyl) anthracene, rubrene, monochloro and dichloro substituted 9,10-bis(phenylethynyl) anthracene, 5,12-bis(phenylethynyl) tetracene, 9,10-diphenyl anthracene, and 16,17-dihexyloxyviolanthrone.

The lifetime and intensity of the chemiluminescent light emitted can be regulated by the use of certain regulators such as: (1) by the addition of a catalyst, which changes the rate of reaction of hydroperoxide. Catalysts which accomplish that objective include those described in M. L. Bender, Chem. Revs., Vol. 60, p. 53 (1960). Catalysts can also be used which alter the rate of reaction or the rate of chemiluminescence including those accelerators of U.S. Pat. No. 3,775,366, and decelerators of U.S. Pat. Nos. 3,691,085 and 3,704,231, or (2) by the variation of hydrogen peroxide. Both the type and the concentration of hydrogenperoxide are critical for the purposes of regulation.

Of the catalysts tried, sodium salicylate and various tetraalkylammonium salicylates have been the most widely used. Lithium carboxylic acid salts, especially lithium salicylate, lithium 5-t-butyl salicylate and lithium 2-chlorobenzoate are excellent catalysts for low temperature hydrogen peroxide/oxalate ester/fluorescer chemiluminescent systems.

As outlined hereinabove, chemical light is produced by mixing reagents e.g., an oxalate ester and hydrogenperoxide together in the presence of a catalyst and a fluorescer. Typically, fluorescers are chosen that are peroxide stable to provide a long lasting glow. In most instances, a single fluorescer has been used to produce a particularly colored light. In some cases, two or more fluorescers of essentially equivalent stability in peroxide have been mixed to produce a blended color. As an example, a blue emitting fluorescer will be mixed with a red emitting fluorescer to make a pink light.

Of the numerous fluorescers described herein, relatively few emit light in peroxyoxalate chemiluminescence and are sufficiently peroxide stable (five phenylethynyl anthracenes, one violanthrone, and three perylene dicarboximides) to yield commercially viable products. While other fluorescers are known to emit light they are not peroxide stable, and have historically been rejected for commercial use. See U.S. Pat. No. 6,267,914. All publications and patents are herein incorporated by reference to the same extent as if each individual publication or patent was specifically and individually indicated to be incorporated by reference.

Figure 6:
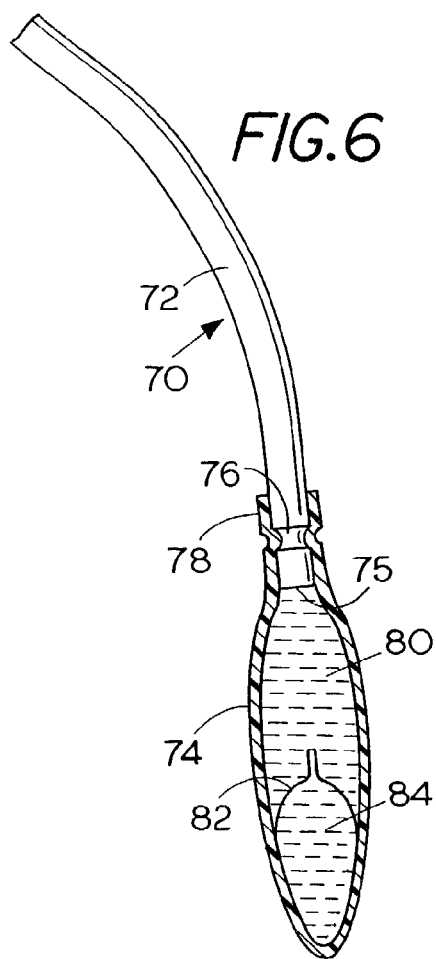
FIG. 6 is a partial longitudinal sectional view of another light energy distribution head on a greatly enlarged scale.

Refer now to FIG. 6 which illustrates another embodiment of the invention employing chemiluminescence. In FIG. 6, the fiber optic bundle 14 is replaced by a flexible shaft or cable 72 formed from solid metal or plastic such as stainless steel or polyester or polyamide plastic which is threaded into the vessel that requires treatment in the same manner described above in connection with the fiber optic bundle 14. At the distal end of the unit is a light distribution head 74 comprising a flexible capsule formed from transparent plastic typically about 1–3 mm in diameter but which is shown greatly enlarged in the figure. The capsule is attached securely to the distal end 75 of the cable 72 over a circular groove 76 into which the upper end 78 of the capsule is tightly pressed. Within the capsule are a chemiluminscent liquid 80 and a small rupturable pouch 82 that can be made from plastic film containing a different reactive chemiluminescent liquid 84. The light producing shaft and head assembly which is indicated generally at 70 is stored indefinitely in the condition shown in the figure until just before use at which time pressure is applied manually to the head 74 causing the sidewalls to be deflected inwardly rupturing the pouch 82 and allowing the liquids 80 and 84 to mix and react chemically so as to luminesce within a blood vessel while positioned as shown in FIG. 3. The capsule 74 which serves as a light distribution head is placed in the area that is narrowed by the plaque formation 22A of FIG. 3. The liquid within the capsule continues to luminesce during the time period required for treatment so that light radiation of the wavelength selected bathes the diseased tissue in light which penetrates the plaque formation and the walls of the surrounding artery or other vessel thereby debilitating or killing the microorganisms within the plaque and surrounding tissue.

Figure 7:
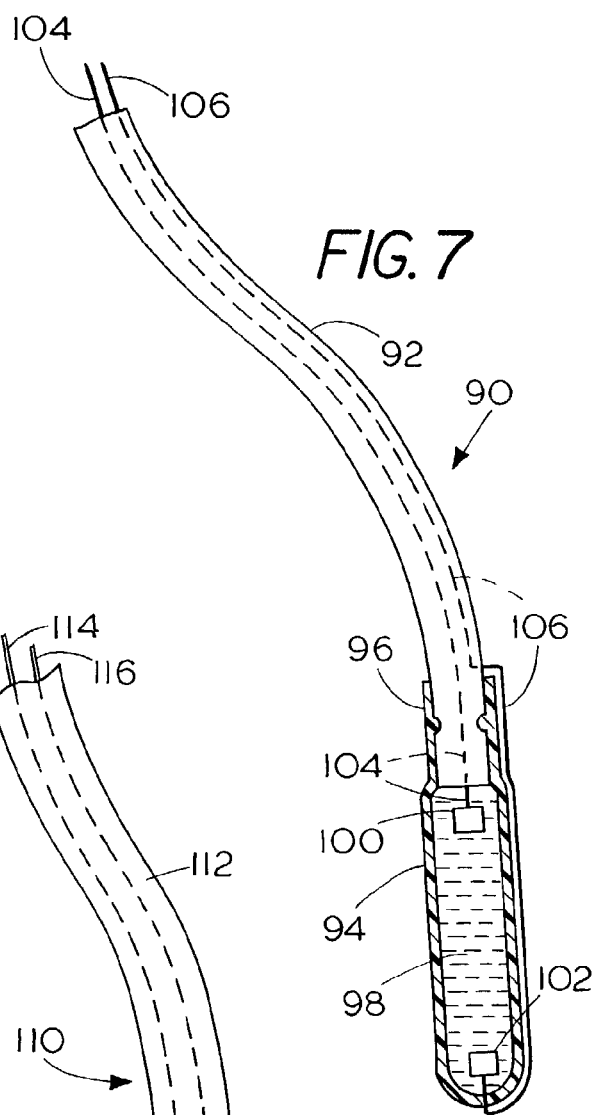
FIG. 7 is a partial longitudinal sectional view of another form of energy distribution head on a greatly enlarged scale and FIG. 8 is a greatly enlarged partial longitudinal sectional view of another form of light energy distribution head in accordance with the invention.

Refer now to FIG. 7, which illustrates another form of a light-producing head 90 in accordance with the invention. In this case, a flexible, elongated and solid shaft or cable 92 has a hollow capsule 94 formed from a transparent plastic material fastened securely at 96 to its distal end. Within the hollow capsule 94 is an electroluminescent liquid chemical 98 of a suitable commercially available composition. Located in spaced apart positions at the ends of the capsules 94 are a pair of electrodes 100 and 102 to which electric current is supplied through conductors 104 and 106 at the upper portions of which extend through the cable 92 to an external electrical power source (not shown) that is used to provide an electric current to the electrodes 100 and 102 so as to excite the electroluminescent chemical 98 causing the liquid to luminesce while the electric current is being applied. As described hereinabove, the light produced by the capsule penetrates into the atherosclerotic plaque or tissue so as to debilitate or kill the microorganisms therein without substantial damage, ablation or destruction of the host tissue, i.e., the body tissue of the patient. The capsule is allowed to remain in the vessel being treated for as long as required to accomplish the desired destruction of the microorganisms.

Figure 8:
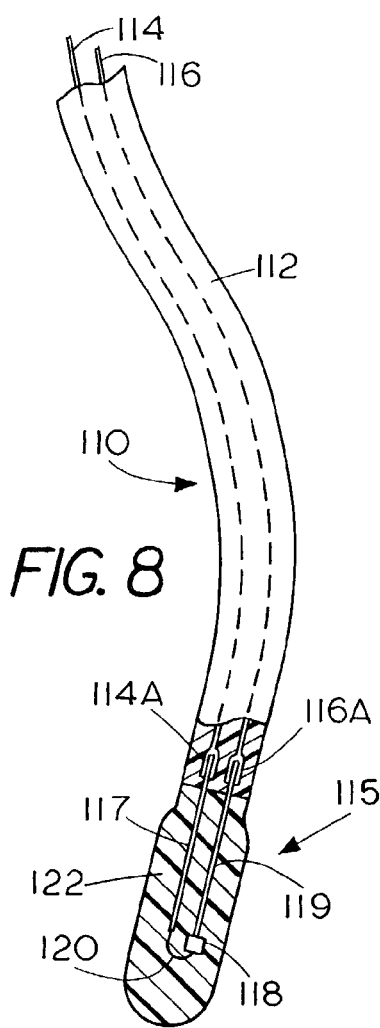

Refer now to FIG. 8. which illustrates another light producing device 110 for treating atherosclerosis including a flexible plastic shaft or cable 112 similar to cable 92. Extending throughout the length of the cable 112 are electrical conductors 114, 116 which terminate at their distal ends in sockets 114A and 116A. Mounted on the distal end of the cable are one or more light emitting diodes (LED), in this case one indicated generally by the numeral 115. Light emitting diode 115 has a pair of power supply contacts 117 and 119 which are plugged into the sockets 114A and 116A, a semiconductor chip 118 and a contact wire 120 which extends from the chip 118 to the contact 117. The contacts and chip are in this case embedded within a solid transparent plastic casing 122 such as epoxy plastic. The diameter of the casing 122 is made small enough e.g. about 1–3 mm in diameter so that it can be inserted into the vessel that requires treatment. Once inserted, a current is supplied to the conductors 114 and 116 causing the LED to provide light of a selected spectral range most preferably blue light in the range between about 300–500 nm or red light of about 600–800 nm or the combination thereof. An important advantage of the LED 115 is its ability to provide cool light radiation that is highly effective in destroying the microorganisms present in the plaque and surrounding vessels without damaging the tissue of the patient. The LED is turned on and allowed to remain in place for a period of time required for effective treatment so as to achieve light sterilization of the atherosclerotic vascular disease or tissue. If desired, the semiconductor chip 118 can be replaced by a light emitting plastic (LEP) in which the semiconducting material is organic. Any suitable commercially available organic semiconducting material such as a PPV polymer or derivative thereof can be used. During use, the chemical composition of the PPV polymer changes with associated changes in physical and electrico-optical properties that produce light radiation. If desired, multiple LED's wired to a single power source can be used. Laser diodes can also be used if desired.

Another general objective of the invention is to be able to treat coronary artery disease (CAD), periodontal disease, as well as atherosclerotic vascular disease and associated vascular inflammation in a non-invasive way, i.e., from a part of the body that is visible and accessible externally and which can be considered, from a clinical standpoint, to be on the exterior of the body, specifically, the mouth, teeth, and gums, all of which are exteriorly accessible and can be treated non-invasively. Thus, when viewed from the manner in which therapy is applied, the mouth, teeth, and gums are not internal organ of the body and therefore can be treated even by the patient himself in some cases without the presence of a health-care worker or direct medical supervision, i.e., by the patient at home. The mouth, teeth, gums, and tongue will therefore be referred to as an exteriorly accessible body surface.

Formerly diets heavy in fats such as cholesterol and smoking were considered to be the primary causative agents in coronary artery disease (CAD). It is now recognized that generalized systemic inflammation, i.e., those originating within chronic inflammatory states, e.g., chronic gum disease, can predispose the patient to changes in the arteries which lead to atherosclerotic lesions. It has also been recognized recently that microorganisms arising from chronic inflammatory or infectious conditions such as chronic gum disease are carried through the bloodstream to the heart and that the microorganisms transferred in this way change conditions in the artery walls which lead to the lesions in which cholesterol deposits or plaque is formed within the wall of the artery. While these generalized infections have been suspected as a causative factor for the last few years, it is now recognized that microorganisms themselves, or the associated systemic inflammation caused by chronic infection, are an important causative agent in coronary artery disease. More specifically, the *Porphyromona gingivalis* bacterium has been traced passing to the blood supply through the coronary artery. An important objective of the present invention is to find a way of reducing or eliminating CAD by reducing generalized infections and especially those associated with periodontal disease.

The aspect of the present invention which will be described in connection with FIGS. 9–17 concerns the treatment of atherosclerotic vascular disease and the associated vascular inflammation and plaque by reducing infections in parts of the body other than in the heart such as the mouth and especially through the treatment of periodontal disease by killing or debilitating pathogenic microorganisms in and around the gum tissue surrounding the teeth, especially *Porphyromona gingivalis*, a bacterium linked to gum disease as well as any other pathogenic microorganisms that are present in the mouth through the application of light energy in an amount sufficient to kill or otherwise debilitate the pathogenic microorganisms in the mouth. While chronic gum disease can lead to the loss of teeth, there is now convincing evidence that infections in the mouth spread from the mouth into the bloodstream and ultimately into the aorta and coronary arteries where they cause inflammation and contribute to the development of atherosclerosis and atherosclerotic plaque. For many years periodontal disease has been recognized as a chronic condition found in a large segment of the population. It is now becoming more apparent because of the bleeding that takes place when the teeth are brushed, that bacteria enter the bloodstream and are carried to the heart. Clinical studies have recently shown that *Porphyromona gingivalis* is present in atherosclerotic lesions, and that periodontal infections contribute to the multiple-pathogen burden present in coronary artery disease (CAD). In this aspect of the invention, the general approach is therefore to reduce or eliminate the symptoms of atherosclerotic vascular disease and the related vascular inflammatory disease and plaque formation by exposing the mouth and especially the gums and the surrounding tissue to light energy in an amount sufficient to kill or debilitate the pathogenic microorganisms associated with periodontal disease. The present invention is also useful in treating the gum disease itself by killing the microorganisms that are responsible and also by decreasing inflammation.

Visible light is especially useful, but the light energy applied in accordance with the invention also includes ultraviolet light and infrared light. When visible light is used, it is particularly effective to employ blue light or red light which will penetrate the gums to a depth of about 2 mm to 6 mm. Visible light is believed to be effective because bacteria, and particularly *Porphyromona gingivalis* contains endogenous porphyrins which are activated by the blue or red light energy. The blue light energy when applied to the teeth and gums will excite the porphyrin ring compounds present in the bacteria. In the presence of oxygen, free radicals will then be generated which are believed to be ultimately be responsible for the death or debilitation of the cell through apoptosis necrosis or other causes. Red light has also been proposed to decrease inflammation by acting directly on the inflamed cells.

In accordance with the present invention, several different light sources can be employed, including but not limited to incandescent light sources, gas discharge tubes, light emitting diodes (LED), laser diodes, chemiluminscent sources, mercury vapor tubes and other light sources known in the art. Light emitting diodes and chemiluminescent sources are particularly useful because they are capable of producing cool light, i.e., light that does not generate sensible heat. When a chemiluminescent source is used, it can be used as described above by focusing the light on the dental tissue, or provided by an appliance in accordance with the present invention in the form of a patch, a sheet, or a molded tray shaped to fit the inner and outer surfaces of the teeth and gums. The tray or sheet form is worn by the patient for a period of time to produce light energy in the mouth in an amount effective to kill the bacteria that cause the periodontal disease or other possible infections within the mouth. The molded tray, sheet, or patch can be constructed in accordance with the invention to provide one or more LED's as a light source or if desired, a gas discharge tube or incandescent light source is placed within the mouth for killing bacteria in the mouth to thereby reduce or eliminate the symptoms of coronary artery disease (CAD), atherosclerotic vascular disease and vascular inflammatory disease.

The invention will now be described further by way of example, in connection with FIGS. 9–11 which show a light-producing appliance 100 in accordance with the invention that consists of a pair of flexible patches in sheet form designated 102 and 104 typically about 1–3 mm in thickness, about 3 cm in width and about 10 cm in length having rounded ends 114 and 116. The patches 102, 104 are formed from any suitable biocompatible material 106 such as a polyolefin, flexible plasticized vinyl resin or of any suitable rubber such as silicone rubber or of any other suitable flexible plastic or rubber compound known in the art which is transparent to light and free of pigment. Uniformly dispersed within the flexible plastic resin or rubber matrix 106 is chemiluminescent agent of any of the compositions described hereinabove or of any other suitable chemiluminescent composition known in the art for producing light energy for irradiating the mouth and especially the upper and lower gums 110, 112 respectively (FIG. 10.). Thus, the appliance consists of two sheets or strips 102, 104 one of which is placed just inside the teeth, i.e., between the teeth and the tongue, and the other 104 is placed within the mouth between the teeth and the lips and are allowed to remain in place for a period of time which is sufficient for killing the microorganisms which may be a few minutes to several hours as the light energy produced by the chemiluminescent agent within the patches or strips 102, 104 radiates the mouth tissue and especially the gum tissue at the base of the teeth so as to kill pathogenic microorganisms that are present and especially the *Porphyromona gingivalis* as well as other bacteria present in the pockets that characterize periodontal disease. The *Porphyromona gingivalis* which has been found particularly closely linked with the CAD, atherosclerotic vascular disease and the accompanying plaque-filled lesions associated with atherosclerosis of the coronary arteries is killed or debilitated directly by the light energy, thereby reducing or eliminating the symptoms of atherosclerotic vascular disease and accompanying vascular inflammation.

In order to hold the inner and outer patches 102, 104 in place, for example, during sleep, they are optionally provided with a coating layer of adhesive shown at 104a and 102a respectively (FIG. 10) for anchoring them to inner and outer surfaces of the gums and teeth. The adhesive 102a, 104a can comprise any suitable medical grade adhesive, but is preferably a hydrogel adhesive, i.e., a water-based medical adhesive such as an adhesive containing moisture, together with a hydrophilic polymer, e.g., polyacrylamide, or a gum such as karaya gum or other suitable gum such as guar gum, carboxymathyl cellulose or carboxypropyl cellulose with or without a humectant such as glycerin. Both the resin 106 and the adhesive 102a, 104 are preferably transparent so that the light produced within the appliance 100 will pass easily into the body tissue. In order to direct all of the light toward the gums, the surfaces thereof furthest from the gums and teeth can be made reflective, e.g., by coating them with a reflective aluminum foil layer (not shown).

As described thus far, the appliance 100 consists of two separate patches. However, if desired the two patches that make up the appliance can be connected together to form one integral appliance by the provision of a horizontally disposed U-shaped connecting layer 108 which is molded integrally with the strips 102, 104 as they are formed to define a biting surface between the teeth, i.e., to define a tray having upper and lower channels for the teeth as shown in FIG. 10.

During use, the appliance 100 is placed in the mouth for a period of time, which is sufficient to kill the microorganisms. While the chemiluminescent agent produces only a few milliwatts of light energy, the exposure time is sufficient so that the light energy striking the *Porphyromona gingivalis* bacteria or other pathogenic microorganisms present is selectively absorbed, especially by the porphyrin ring compounds present so as to debilitate or kill the bacteria directly by exciting molecular constituents that are present to produce free radicals capable of killing the microorganisms without noticeable damage or destruction of the patient's own body tissue. After a sufficient treatment time of, say, 10 minutes to six hours the patient removes the appliance 100 from the mouth. This process can be repeated daily, weekly or at other intervals in order to maximize the effects and prevent further infections. As a result of the radiation produced by the appliance, the bacterial count associated with the periodontal disease present in the patient's gums is substantially reduced or eliminated thus improving the health of the teeth, but even more importantly, reducing the bacterial load that would otherwise be transferred through the blood stream to the coronary arteries and associated vessels, thereby providing and effective treatment for reducing or eliminating the symptoms of CAD, atherosclerotic vascular disease and associated vascular inflammation. For convenience, the appliances 100 whether trays or patches can be provided in different sizes, such as small, medium, and large. When constructed as a patch, it is suitable as a single-use, disposable item. When constructed as a heavier, more substantial unit such as a tray with upper and lower channels it can be used repeatedly. The chemiluminescent agent can be activated in any suitable manner, e.g., by exposing the appliance 100 to a suitable catalyst or to light energy, e.g., by placing it next to a lamp before it is used.

Figure 9:
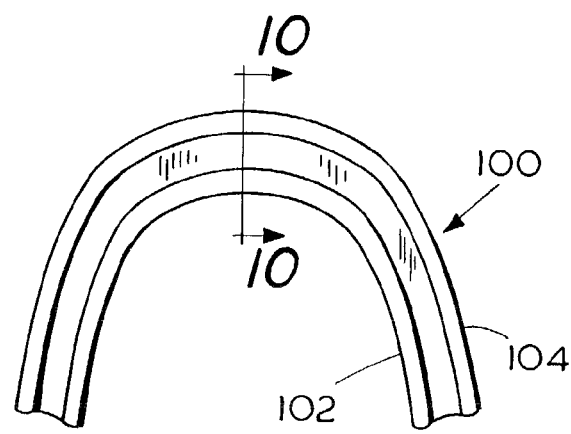
FIG. 9 is a top plan view of a medical appliance for treating vascular disease and more particularly atherosclerotic vascular disease.
Figure 10:
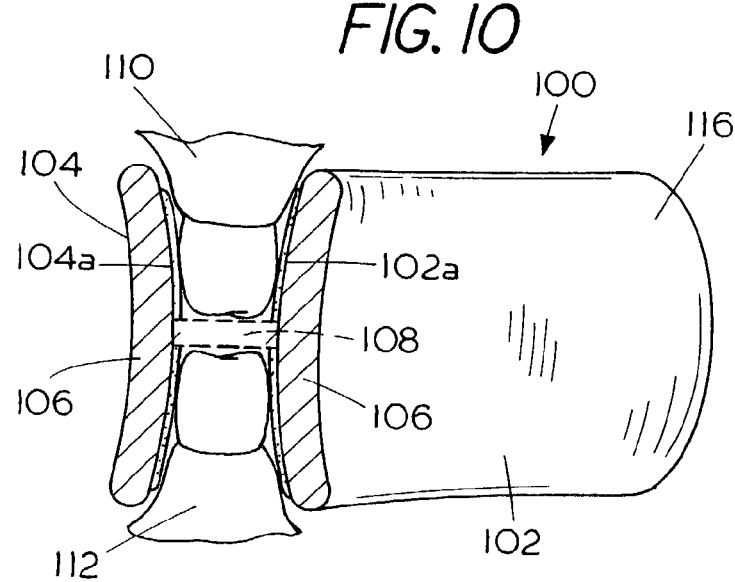
FIG. 10 is a vertical cross-sectional view taken on line 10—10 of FIG. 9 on an enlarged scale.
Figure 11:
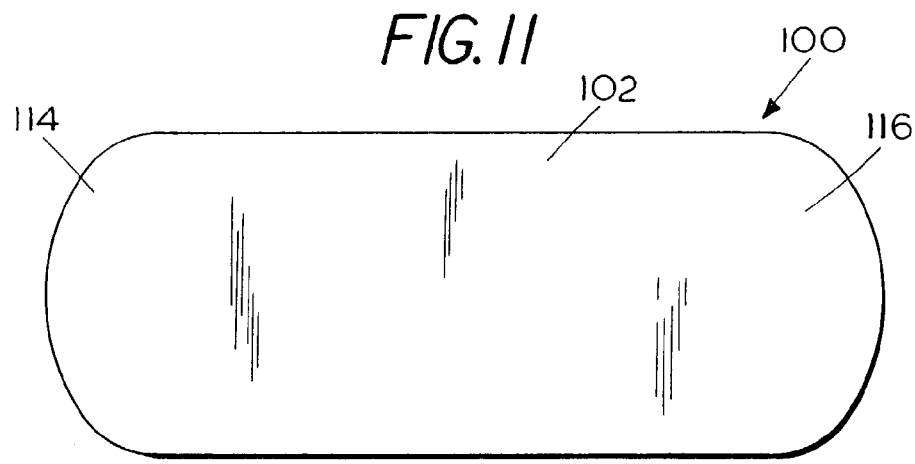
FIG. 11 is an elevational view of the appliance of FIGS. 9 and 10 with the appliance in a flattened condition prior to use.
Figure 12:
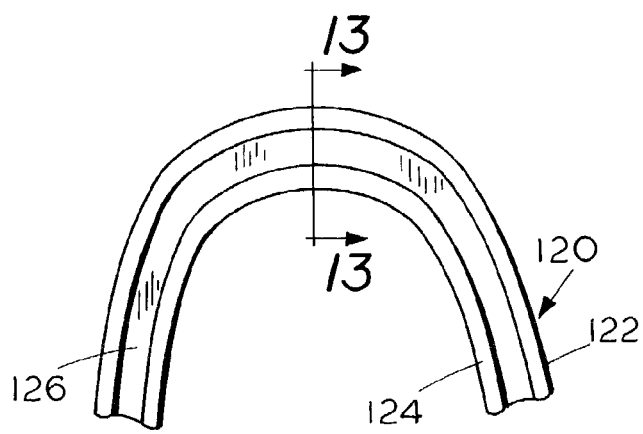
FIG. 12 is a top plan view of an appliance in accordance with another embodiment of the invention.
Figure 13:
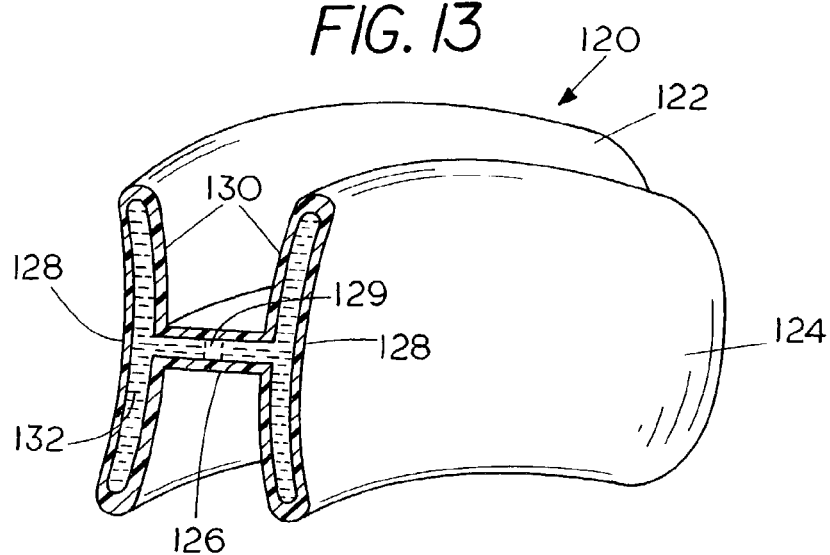
FIG. 13 is a vertical sectional view taken on line 13—13 and FIG. 12 on an enlarged scale.

Refer now to FIGS. 12 and 13 which illustrate another embodiment of the invention comprising a tray 120 of the same general size and shape of that shown in FIGS. 9–11 and constructed of a similar matrix composed of transparent flexible plastic resin or rubber material in the form of outer and inner strips 122, 124 that are hollow throughout and include centrally facing opposing walls 130 on the inside and outwardly facing walls 128 (FIG. 13) that touch the lips and the tongue during use. Inner and outer portions are connected by a hollow horizontal generally U-shaped biting chamber 126. Contained within the appliance 120 is a chemiluminescent liquid 132 which produces light energy, especially visible light such as blue or red visible light for irradiating the bacteria and other pathogenic microorganisms found within the surrounding body tissue of the patient, thereby sterilizing the tissue. Preferably, a removable barrier 129 comprising a rupturable sheet of plastic or rubber is provided within the appliance 120 to divide the appliance into two separate chambers on either side thereof to keep two chemically reactive, potentially luminescent chemical agents separated until just before use. There can be a reflecting surface on the side opposite the treating surface in order to direct the light toward the treating surface adjacent the body tissue. When the appliance 120 is to be used, the patient merely squeezes or strikes the tray, rupturing the membrane 129 thereby allowing liquid that is present in the outer chamber 122 to mix with and react chemically with liquid that is present on the opposite side of the barrier 129 within the chamber 124. As soon as the two liquids react chemically, the chemiluminescent agent is formed which then begin to irradiate the body tissue of the patient with light energy which is sufficient during the period of use, e.g., overnight, to be absorbed directly by the microorganisms to kill or debilitate them, thereby sterilizing the mouth and in turn killing microorganisms that would otherwise be transferred through the circulatory system to the heart and related tissue so as to reduce or eliminate the symptoms of CAD, atherosclerotic vascular disease, vascular plaque, and vascular inflammation. The light produced can be any suitable visible light, especially red light or blue light in the range of 300–500 nm peaking about 400 nm to 430 nm. When red light is used, it typically has a wavelength in the range of about 600–800 nm with a peak in the range of about 630–650 nm or a combination of these lights.

The light patches can also be held in place with the use of a clear dental tray (not shown) molded to fit the teeth and gums of the patient. The tray can be provided with a slot on the exterior surface to hold the patches. The tray can be reusable or single use.

Figure 14:
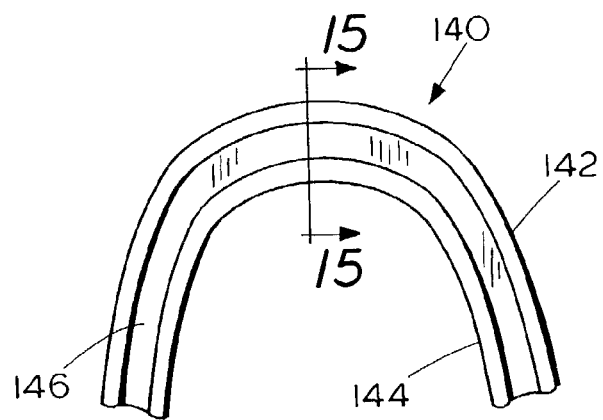
FIG. 14 is a plan view of another form of the invention.
Figure 15:
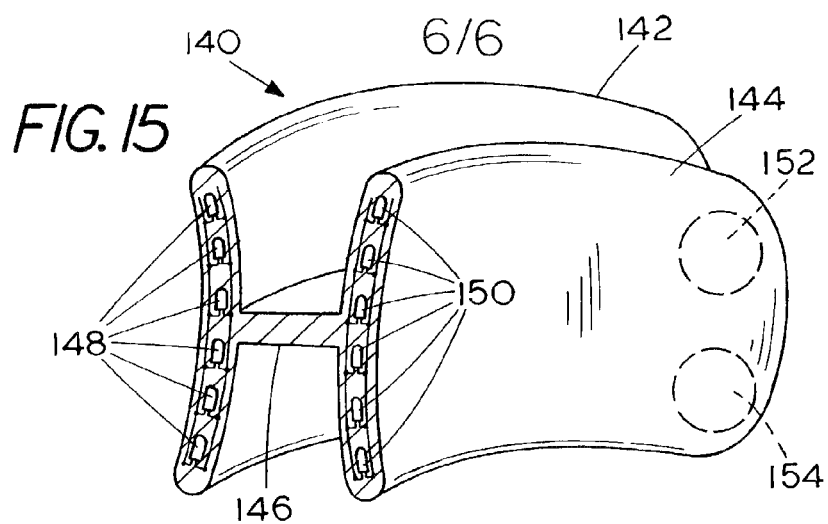
FIG. 15 is a vertical sectional view taken on line 15—15 of FIG. 14 on an enlarged scale.
Figure 16:
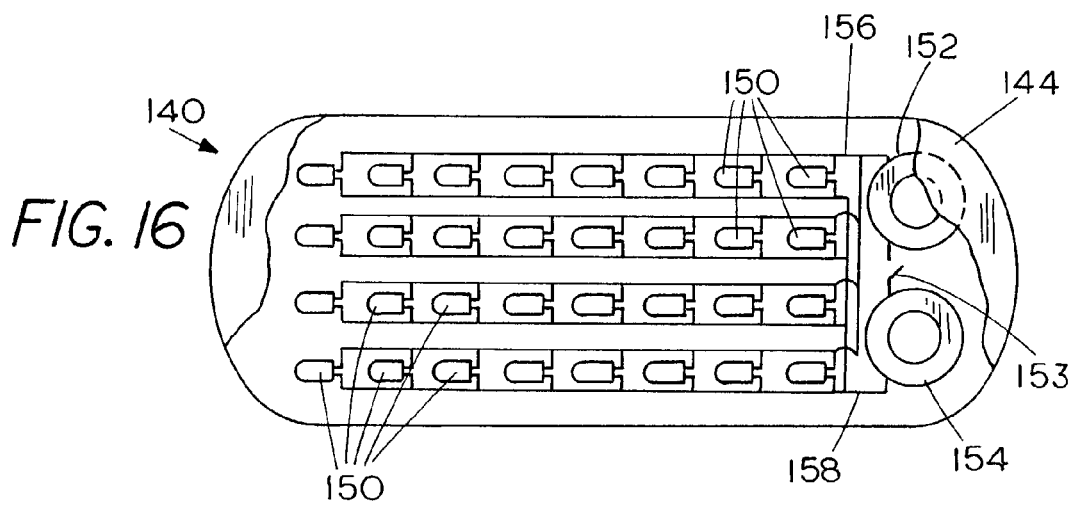
FIG. 16 is an elevational view of the appliance of FIG. 15 as seen in a flattened condition and FIG. 17 is a diagrammatic side-elevational view of another form of the invention as seen during use.

Refer now to FIGS. 14–16 which show a U-shaped dental tray 140 comprising a matrix of a flexible plastic resinous or rubber material such as silicone rubber that includes an outer strip 142, an inner strip 144, a multiplicity of light emitting diodes (LED's) 148 and 150 all of which are wired by means of electrical conductors sets 156 and 158 to a suitable power source such as the batteries 152, 154 (FIGS. 15 and 16) controlled by means of an on/off switch 153 which can be a toggle switch extending slightly from the surface of the rubber tray so that the user can turn the switch on just before use thereby energizing the LED's for producing light energy to kill the bacteria especially *Porphyromona gingivalis* associated with periodontal infections within the adjacent gum tissue. The surfaces of the tray that are away from the gums can be coated with a reflective material such as silver or aluminum that is embedded within the rubbery matrix into which the LED's 148, 150 are molded.

To use the appliance 140 of FIGS. 14–16, the switch 153 is closed. The tray 140 is then placed in the mouth with the upper row of teeth in the upper channel and the lower row of teeth in the lower channel separated by the horizontal U-shaped strip 146 which is integral with the rest of the tray. Tray 140 is allowed to stay in the mouth, preferably overnight, for killing the microorganism within the mouth so as to thereby reduce or eliminate the symptoms of periodontal disease, CAD, atherosclerotic vascular disease and the associated vascular inflammation and atherosclerotic plaque.

While suitable LED's that are capable of producing visible light in any portion of the spectrum can be employed, LED's producing red light within the general range of from about 600–800 nm with a peak at 630–650 nm can be used, but most preferably blue light is used with a typical range of from about 300–500 nm with a most preferred range of about 400–430 nm. These light sources can be used in combination. When the power supply consists of midget batteries, only a fraction of the watt will be produced but if an external power supply (not shown) is provided, the tray 140 can produce 30–50 or more watts of power. Illuminous flux that results is capable of penetrating the gum tissue 2 mm or more, reducing the bacterial count to a low level within a period of as little as an hour or two, thereby reducing or eliminating the symptoms associated with CAD, atherosclerotic vascular disease, vascular inflammation and plaque. If desired, the tray 140 can be composed of an opaque plastic or rubber compound with a hole (not shown) therein surrounding each LED for allowing the light to reach the gum tissue.

Figure 17:
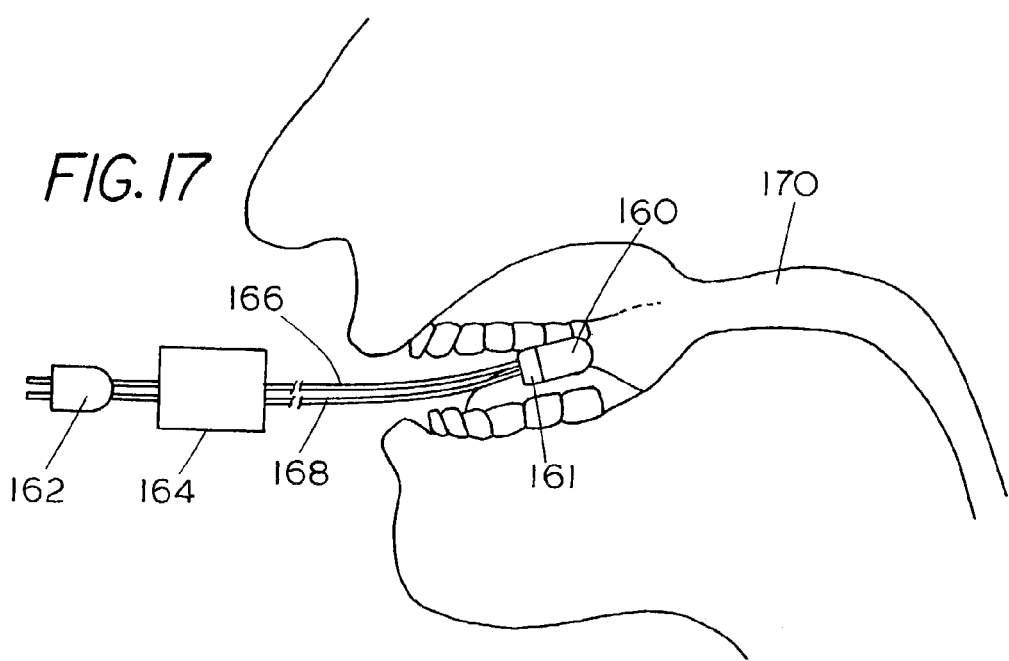

Refer now to FIG. 17 which shows another embodiment of the invention, in this case an incandescent electric light bulb 160 that is secured to a socket 161 to which current is supplied from a wall plug 162 through a step-down transformer 164 wired to the bulb socket 161 through insulated conductors 166, 168 which typically carry about 12 volts to the bulb 160. The bulb 160 can be any suitable source of light radiation such as an incandescent electric bulb, a gas discharge bulb, mercury vapor bulb, or the like as described for example in U.S. Pat. No. 6,464,625 or in pending U.S. patent application Ser. Nos. 09/598,653 or 10/119,976 all of which are incorporated herein by reference. During use, the bulb 160 is placed in the mouth so as to provide light radiation throughout a wide spectrum. Most preferably the bulb 160 is enclosed within a filter coating for irradiating the mouth and especially the teeth and gum area with visible light radiation of a selected spectral range, preferably blue light in the range of between about 300–500 nm. Other light spectral ranges can be employed such as red light in the general range of about 600–800 nm for longer periods of exposure or the combination of these wavelengths. The advantage of the appliance of FIG. 17 is that greater power of 40–60 watts or more can be provided to thereby achieve an effective bacterial kill in a much shorter period of time such as 30 minutes of exposure. When the gums are radiated in the manner described two or three times a week, the microorganisms especially *Porphyromona gingivalis* bacterium associated with periodontal disease is reduced to a very low order, which in turn drastically reduces the bacterial load that is transferred via the bloodstream to the heart thus reducing or eliminating the symptoms of CAD, atherosclerotic vascular disease, vascular inflammation, and plaque formation.

If desired, in any of the embodiments of the invention described hereinabove, an optional light-sensitizing medication can be used such as any of the photofrin or other light enhancing compound known to those skilled in the art for preferentially absorbing the light radiation so as to furnish a more effective bactericidal action. One suitable sensitizing agent is aminoleveivinic acid. Another suitable sensitizer comprises a psoralen such as demethylchlortetracycline. Other suitable known sensitizers can be employed if desired. The photosensitizer employed should be matched to the wavelength of the light provided so that the light is absorbed by the particular photosensitizer that is used. Other sensitizing agents will be apparent to those skilled in the art once the principals described herein are understood. The light sensitizing medication can be applied topically to the teeth and gum surfaces, to the vessel walls, or taken orally or by intravenous injection. Although helpful in some situations, photosensitizers are not an essential feature of the invention.

Many variations of the present invention within the scope of the appended claims will be apparent to those skilled in the art once the principles described herein are understood.

The invention claimed is:

1. A method of treating atherosclerotic vascular disease by exposing an exteriorly accessible body surface within the mouth of a patient to light energy for killing or debilitating pathogenic microorganisms within the mouth so as to thereby reduce or eliminate one or more of the symptoms of atherosclerotic vascular disease and associated vascular inflammation and including the step of providing the light energy from a chemiluminescent light emitting article and placing the article proximate to the gums of the patient for killing microorganisms associated with periodontal disease.

2. The method of claim 1 including the step of providing a dental tray that supports the light emitting article.

3. The method of claim 1 including the step of providing the chemiluminescent agent dispersed within a dental tray.

4. The method of claim 1 including the step of providing a source of light energy comprising visible light selected from the group consisting of red light and blue light or the combination thereof.

5. The method of claim 1 including the step of providing a source of light energy comprising ultraviolet light.

6. The method of claim 1 including the step of applying an electrical current across said chemiluminescent agent to facilitate the production of light energy thereby.

7. The method of claim 1 including the step of adhesively bonding the light emitting article to the teeth or gums of the patient to provide said light energy.

8. A method of treating atherosclerotic vascular disease by exposing an exteriorly accessible body surface within the mouth of a patient to light energy for killing or debilitating pathogenic microorganisms within the mouth so as to thereby reduce or eliminate one or more of the symptoms of atherosclerotic vascular disease and associated vascular inflammation and wherein the wavelength of the light is selected from the group consisting of ultraviolet light of about 200–400 nm and blue visible light of about 300–500 nm or a combination thereof without damage, destruction or ablation of the body tissue of the patient.

9. The method of claim 8 wherein a light-sensitizing medication is administered to the patient prior to exposing the body surface to light energy.

10. The method of claim 9 wherein the light-sensitizing medication is applied topically to the teeth and gum surfaces, to the vessel walls or taken orally or by intravenous injection.

11. The method of claim 8 including the step of providing a light emitting diode for producing said light energy and applying an electric current to the diode.

12. A method of treating atherosclerotic vascular disease by exposing an exteriorly accessible body surface within the mouth of a patient to light energy for killing or debilitating pathogenic microorganisms within the mouth so as to thereby reduce or eliminate one or more of the symptoms of atherosclerotic vascular disease and associated vascular inflammation and including the step of providing a flexible patch that is sized and constructed with a source of light radiation supported thereon and irradiating the gum tissue of the patient with light energy from the patch to kill bacteria responsible for periodontal disease.

13. A method of treating atherosclerotic vascular disease by exposing an exteriorly accessible body surface within the mouth of a patient to light energy for killing or debilitating pathogenic microorganisms within the mouth so as to thereby reduce or eliminate one or more of the symptoms of atherosclerotic vascular disease and associated vascular inflammation and including the step of providing a hollow dental appliance containing a chemiluminescent liquid therein to provide the light energy.

14. The method of claim 13 including the step of providing the dental appliance with a removable barrier for separating two chemically reactive agents that produce said chemiluminescent liquid when the barrier is removed so as to allow the agents to be mixed and to react chemically with one another.

15. A method of treating atherosclerotic vascular disease by exposing an exteriorly accessible body surface within the mouth of a patient to light energy for killing or debilitating pathogenic microorganisms within the mouth so as to thereby reduce or eliminate one or more of the symptoms of atherosclerotic vascular disease and associated vascular inflammation and including the step of providing as a dental appliance a dental tray and a plurality of light emitting diodes that are supported thereby for producing the light energy.

16. The method of claim 15 wherein the light emitting diode is a laser diode.

17. A method of treating vascular inflammation associated with atherosclerotic vascular disease by exposing an exteriorly accessible body surface within the mouth of a patient to chemiluminescent light energy for diminishing inflammation within the mouth so as to thereby reduce or eliminate one or more of the symptoms of vascular inflammatory disease without damage, destruction or ablation of the wall of the an exposed vessel or the surrounding body tissue.

18. The method of claim 17 wherein a light-sensitizing medication is administered to the patient prior to exposing the body surface to light energy.

19. The method of claim 18 wherein the light-sensitizing medication is applied topically to the teeth and gum surfaces, to the vessel walls or taken orally or by intravenous injection.

20. A method of treating atherosclerotic vascular disease by applying light energy to a selected portion of the body of the patient where microorganisms associated with atherosclerotic vascular disease are located comprising, providing an instrument that furnishes light energy from a light source, providing said light energy at a wavelength between about 200–500 nm comprising cool light substantially without heat that can be sensed, providing on said instrument an operating member to direct the light energy for application to the body of the patient, applying the light energy from the operating member to an exteriorly accessible body surface of the patient that can be exposed non-invasibely where pathogenic microorganisms associated with atherosclerotic vascular disease are located to thereby kill or debilitate the pathogenic microorganisms thereon that are associated with atherosclerotic vascular desease without damage, destruction, or ablation of the body tissue of the patient and, the death of the microorganisms reducing or eliminating one or more of the symptoms of coronary artery disease, atherosclerosis, vascular inflammation, or vascular plaque formation.

21. The method of claim 20 wherein the exteriorly accessible body surface of the patient comprises the mouth of the patient and, applying light energy comprising cool light having a wavelength between about 200 nm–500 nm to the mouth of the patient.

22. The method of claim 20 wherein the exteriorly accessible body surface comprises the mouth of the patient, and applying the light energy to the patient's mouth for killing or debilitating pathogenic microorganisms within the mouth of the patient, comprising *Porphyromona gingivalis* bacteria.

23. A method of treating vascular disease by the application of light energy comprising, providing an instrument that furnishes light energy from a light source, providing on said instrument an operating member to direct the light energy for application to the body of the patient, applying the light energy from the instrument to a selected portion of the body tissue where pathogenic microorganisms are located that are associated with a vascular disease selected from the group consisting of atherosclerotic vascular disease, coronary artery disease, and vascular inflammatory disease, providing the light energy in an amount sufficient to reduce inflammatory cytokines, inflammatory chemokines, and to kill or debilitate pathogenic microorganisms without damage, destruction, or ablation of the body tissue of the patient, thereby reducing or eliminating one or more of the symptoms of coronary artery disease, atherosclerotic vascular disease or vascular inflammatory disease.

24. The method of claim 23 wherein said microorganisms are pathogenic microorganisms selected from the group consisting of Cytomegalo virus, *Chlamydia, Helicobacter pylon, Porphormona gingivalis*, and herpes virus.

* * * * *